(12) United States Patent
Tokumoto et al.

(10) Patent No.: US 8,419,708 B2
(45) Date of Patent: Apr. 16, 2013

(54) TRANSDERMAL DRUG ADMINISTRATION APPARATUS HAVING MICRONEEDLES

(75) Inventors: Seiji Tokumoto, Tsukuba (JP);
Toshiyuki Matsudo, Tsukuba (JP);
Tetsuji Kuwahara, Tsukuba (JP)

(73) Assignee: Hisamitsu Pharmaceuticals Co., Inc., Saga (JP)

( * ) Notice: Subject to any disclaimer, the term of this patent is extended or adjusted under 35 U.S.C. 154(b) by 441 days.

(21) Appl. No.: 12/278,483

(22) PCT Filed: Feb. 7, 2007

(86) PCT No.: PCT/JP2007/052143
§ 371 (c)(1),
(2), (4) Date: Aug. 6, 2008

(87) PCT Pub. No.: WO2007/091608
PCT Pub. Date: Aug. 16, 2007

(65) Prior Publication Data
US 2009/0030365 A1    Jan. 29, 2009

(30) Foreign Application Priority Data
Feb. 10, 2006   (JP) .................................. 2006-034483

(51) Int. Cl.
*A61M 31/00*   (2006.01)

(52) U.S. Cl.
USPC ............... 604/506; 604/21; 604/22; 604/272; 604/500

(58) Field of Classification Search ............ 604/21, 604/22, 173, 272, 506, 27, 28, 70, 500; 427/2.3
See application file for complete search history.

(56) References Cited

U.S. PATENT DOCUMENTS

| 4,573,996 A | 3/1986 | Kwiatek et al. |
| 4,842,577 A | 6/1989 | Konno et al. |
| 5,250,023 A | 10/1993 | Lee et al. |

(Continued)

FOREIGN PATENT DOCUMENTS

| JP | 5084180 B | 12/1993 |
| JP | 6014980 B | 3/1994 |

(Continued)

OTHER PUBLICATIONS

Raccach M., et al, Manganese and Lactic Acid Bacteria, J. Food Prot., Oct. 1985, vol. 48, No. 10, p. 895-898.

(Continued)

*Primary Examiner* — Bhisma Mehta
*Assistant Examiner* — Imani Hayman
(74) *Attorney, Agent, or Firm* — Sughrue Mion, PLLC

(57) ABSTRACT

It is intended to provide a transdermal drug administration apparatus having microneedles, which is capable of piercing the skin by a simple procedure in the transdermal administration of a biologically active substance (drug) and allows rapid absorption of the biologically active substance. The present apparatus comprises a microneedle device (50) comprising a microneedle substrate (53) having a plurality of microneedles (51) capable of piercing the skin, an absorbent (11) disposed thereon, the absorbent (11) comprising a material capable of absorbing a liquid, and a dissolving solution reservoir (18) disposed on the absorbent (11), the dissolving solution reservoir (18) containing a dissolving solution (16) for dissolving a drug and being capable of disrupting a diaphragm (20) provided the dissolving solution reservoir (18) and the absorbent (11) by pressing. A coating containing a dry drug is disposed on the microneedles (51) and/or the microneedle substrate (53).

2 Claims, 9 Drawing Sheets

U.S. PATENT DOCUMENTS

| | | | |
|---|---|---|---|
| 5,310,404 A * | 5/1994 | Gyory et al. | 604/20 |
| 6,656,147 B1 * | 12/2003 | Gertsek et al. | 604/28 |
| 7,015,262 B2 * | 3/2006 | Leong | 523/205 |
| 7,047,070 B2 | 5/2006 | Wilkinson et al. | |
| 7,963,935 B2 | 6/2011 | Cormier et al. | |
| 2003/0045837 A1 * | 3/2003 | Delmore et al. | 604/173 |
| 2003/0135161 A1 | 7/2003 | Fleming et al. | |
| 2003/0161869 A1 | 8/2003 | Hatanaka et al. | |
| 2003/0187423 A1 | 10/2003 | Wilkinson et al. | |
| 2009/0030365 A1 | 1/2009 | Tokumoto et al. | |
| 2011/0152743 A1 | 6/2011 | Adachi et al. | |

FOREIGN PATENT DOCUMENTS

| | | |
|---|---|---|
| JP | 11-4655 A | 1/1999 |
| JP | 2000512529 A | 9/2000 |
| JP | 2004503341 A | 2/2004 |
| JP | 2004504120 A | 2/2004 |
| JP | 2004505652 A | 2/2004 |
| JP | 2004528900 A | 9/2004 |
| JP | D1216513 | 9/2004 |
| JP | D1216514 | 9/2004 |
| JP | D1216758 | 9/2004 |
| JP | D1216760 | 9/2004 |
| JP | D1221132 | 10/2004 |
| JP | 2005521524 A | 7/2005 |
| WO | 9748440 A1 | 12/1997 |
| WO | 00/74767 A2 | 12/2000 |
| WO | 02/05889 A1 | 1/2002 |
| WO | 0207813 A1 | 1/2002 |
| WO | 03/037405 A1 | 5/2003 |
| WO | 03084595 A1 | 10/2003 |
| WO | 2005016440 A1 | 2/2005 |
| WO | 2005016441 A1 | 2/2005 |
| WO | 2005063331 A1 | 7/2005 |
| WO | 2005/041871 A2 | 5/2010 |

OTHER PUBLICATIONS

Supplementary Partial European Search Report issued on Feb. 17, 2010, in counterpart European application serial No. EP 07 71 3903.

International Searching Authority, "International Search Report," issued in connection with International Patent Application No. PCT/JP2007/052143, dated Apr. 24, 2007.

International Searching Authority, "Written Opinion," issued in connection with International Patent Application No. PCT/JP2007/052143, dated Apr. 24, 2007.

* cited by examiner

TRANSDERMAL DRUG ADMINISTRATION APPARATUS HAVING MICRONEEDLES

TECHNICAL FIELD

The present invention relates to a transdermal drug administration apparatus for administering a drug via the skin. Particularly, the present invention relates to a transdermal drug administration apparatus having microneedles comprising a plurality of microneedles capable of piercing the skin.

BACKGROUND ART

Heretofore, a method has generally been performed which comprises applying an adhesive skin patch containing a drug to the skin and allowing permeation of the drug from this adhesive skin patch to the skin, thereby administering the drug. On the other hand, administration methods using electrical energy, such as iontophoresis (Journal of Pharmaceutical Sciences, Vol. 76, p. 341, 1987) and electroporation (National Publication of International Patent Application No. 1991-502416; and Proc. Natl. Acad. Sci. USA, Vol. 90, p. 10504-10508, 1993), have been developed as methods for promoting drug absorption to the skin or mucous membrane. Iontophoresis and electroporation have both been expected to be utilized as methods for promoting transdermal or transmucosal drug absorption.

In connection with the promotion of drug absorption, National Publication of International Patent Application No. 2000-512529 (Patent Document 1) proposes an apparatus for mechanically piercing the skin before the release of transdermal pharmaceutical agents, thereby enhancing a transdermal flux thereof. This apparatus comprises a sheet having a plurality of openings, a plurality of microblades which are integrally formed therewith and extend downward therefrom, and means for anchoring the apparatus to the body surface. In this case, a dosage form in a pharmaceutical agent reservoir is, for example, an adhesive gel.

This kind of apparatus capable of retaining a drug in a dry form is, for example, a transdermal administration instrument for a protein or peptide drug described in Japanese Patent Publication No. 6-14980 (Patent Document 2), which comprises a skin needle. This instrument has a multilayer comprising an electrode leading to the outside, a polyelectrolyte tank, a hydrophilic polymer drug support, and a water-swellable polymer skin needle support, wherein a solvent inlet is formed in a central portion of the upper end of the polyelectrolyte tank. This solvent inlet is made of, for example, a rubber in the form of a V-shaped groove, through which an ionized solvent composition can be introduced to the inside of the polyelectrolyte tank by use of a syringe or the like. This instrument, when used, requires preparing an additional syringe or the like for introducing a solvent composition.

An apparatus which is capable of retaining a drug in a dry form and requires no syringe or the like is, for example, a transdermal delivery apparatus with a valve described in WO03/084595A1 (Patent Document 3). This apparatus comprises a reservoir capable of retaining, for example, distilled water, a valve for opening and closing this reservoir, a cavity capable of retaining a dry drug, and a plurality of micro skin penetrating members capable of penetrating the skin. This apparatus, when used, is disposed on the skin of a patient and pushed downward such that the micro skin penetrating members can penetrate the skin. Then, the valve is opened, and the reservoir is pressed, whereby the distilled water is supplied to the dry drug, thereby delivering the drug to the patient.

On the other hand, Japanese Patent Publication No. 5-84180 (Patent Document 4) discloses a novel plaster structure for iontophoresis. This plaster structure does not comprise such a skin needle. For example, a capsule filled with an electrolytic solution is provided in an upper portion of this plaster structure. This structure is constituted such that the structure, when applied to the skin, disrupts a thin film such as aluminum foil located between this capsule and a water-containing layer to infiltrate the electrolytic solution thereinto. When a water-soluble drug is used, the plaster structure may respond to a demand as a plaster structure comprising a capsule filled with an electrolytic solution, wherein drug-containing and water-containing layers are adjusted to be in a dry state.

Furthermore, coating techniques for microneedles have recently proceeded in various ways. For example, National Publication of International Patent Application No. 2004-504120 (Patent Document 5) discloses a drug delivery device having a skin piercing member comprising a solid biodegradable reservoir medium containing a drug. This reservoir medium is coated externally on the skin piercing member. As described therein, it is preferred that the reservoir medium should be sugars (lactose, raffinose, trehalose, or sucrose) dissolved by biodegradation to easily release the drug contained therein. Moreover, National Publication of International Patent Application No. 2004-528900 (Patent Document 6) discloses that a coating carrier for a microprojection array used in the transdermal administration of a vaccine or the like is selected from human albumin, polyglutamic acid, polyaspartic acid, polyhistidine, pentosan polysulfate, and polyamino acid. This coating carrier is also rapidly dissolved after skin penetration, thereby releasing a beneficial active substance. Furthermore, WO2005/016440A1 (Patent Document 7) discloses a coating carrier containing a polymer such as hydroxypropylmethylcellulose (HPMC), hydroxypropylcellulose (HPC), dextran, polyvinyl alcohol, or polyethylene oxide. This carrier is flowable with a viscosity of 3 to 500 cps. Therefore, a needle tip is automatically coated with the carrier by designing the needle surface. Thus, as described therein, a coating procedure itself is unnecessary, and the duration of action can be rendered further longer. However, in this case, the coating carrier is forced to penetrate the skin and is therefore difficult to control. Thus, some doubt remains as to its practical use.

Patent Document 1: National Publication of International Patent Application No. 2000-512529
Patent Document 2: Japanese Patent Publication No. 6-14980
Patent Document 3: WO 2003/084595 A1
Patent Document 4: Japanese Patent Publication No. 5-84180
Patent Document 5: National Publication of International Patent Application No. 2004-504120
Patent Document 6: National Publication of International Patent Application No. 2004-528900
Patent Document 7: WO 2005/016440 A1

DISCLOSURE OF THE INVENTION

For retaining a drug in a dry form, transdermal drug administration apparatuses having a skin needle have heretofore required preparing an additional syringe or the like for supplying a liquid to the drug or placing a valve for liquid supply in the apparatus, as described above. Such preparation of an additional syringe or the like complicates the use of the apparatus and sometimes makes it difficult to operate the apparatus by patients themselves. Alternatively, such placement of a valve for liquid supply in the apparatus complicates the apparatus and also increases cost. Aside from this, a method for applying a coating agent containing a drug to microneedles having a needle-like structure is often used in the administration of a vaccine or the like in a trace amount due to the limitation of the amount of a drug administered to an exceedingly small amount and is thus limited in application.

Thus, an object of the present invention is to provide a transdermal drug administration apparatus having microneedles, which is capable of piercing the skin by a simple procedure in the transdermal administration of a biologically active substance (drug) and allows rapid absorption of the biologically active substance.

The object is attained by a transdermal drug administration apparatus having microneedles, comprising a microneedle device comprising a plurality of microneedles capable of piercing the skin and a microneedle substrate having at least one solution passage, a coating disposed on the microneedles and/or the microneedle substrate, the coating containing a dry drug, a pad portion disposed on the microneedle device, and a dissolving solution reservoir disposed on the pad portion, the dissolving solution reservoir containing a dissolving solution for drug dissolution, wherein by pressing the dissolving solution reservoir, the dissolving solution reservoir is opened to supply the dissolving solution to the pad portion and the microneedle device, and further the microneedles pierce the skin, thereby allowing transdermal absorption of the drug dissolved in the dissolving solution. In this context, the transdermal drug administration apparatus having microneedles can further comprise, on the pad portion, an electrode for supplying electrical energy from outside. Alternatively, the transdermal drug administration apparatus having microneedles can further comprise, on the pad portion, a sonic transducer for supplying sonic vibration energy from outside. The microneedle device can comprise, on the microneedle substrate, a plate-like reinforcement having at least one solution passage. Moreover, the pad portion can contain a dry drug. The pad portion can comprise a drug retainer containing the dry drug, and an absorbent for absorbing the dissolving solution.

Moreover, a transdermal drug administration apparatus having microneedles according to the present invention comprises a microneedle device comprising a plurality of microneedles capable of piercing the skin and a microneedle substrate having at least one solution passage, a coating disposed on the microneedles and/or the microneedle substrate, the coating containing a dry drug, an absorbent disposed on the microneedle device, the absorbent comprising a material capable of absorbing a liquid, and a dissolving solution reservoir disposed on the absorbent, the dissolving solution reservoir containing a dissolving solution for dissolving the drug and being capable of disrupting a diaphragm provided between the dissolving solution reservoir and the absorbent by pressing. In this context, the absorbent can contain a dry drug.

Moreover, a transdermal drug administration apparatus having microneedles according to the present invention comprises a microneedle device comprising a plurality of microneedles capable of piercing the skin and a microneedle substrate having at least one solution passage, a coating disposed on the microneedles and/or the microneedle substrate, the coating containing a dry drug, a drug retainer disposed on the microneedle device, an absorbent disposed on the drug retainer, the absorbent comprising a material capable of absorbing a liquid, and a dissolving solution reservoir disposed on the absorbent, the dissolving solution reservoir containing a dissolving solution for dissolving the drug and being capable of disrupting a diaphragm provided between the dissolving solution reservoir and the absorbent by pressing. In this context, the drug retainer can contain a dry drug.

In this context, the transdermal drug administration apparatus having microneedles can further comprise, on the absorbent, an electrode for supplying electrical energy from outside. As a result, the transdermal drug administration apparatus having microneedles can be used as an apparatus for an electrical drug administration system, for example, an apparatus for an iontophoresis system (iontophoresis electrode structure). Alternatively, the transdermal drug administration apparatus having microneedles can further comprise, on the absorbent, a sonic transducer for supplying sonic vibration energy from outside. In this case, the plurality of microneedles can have a hollow passage capable of delivering the drug in the longitudinal direction thereof, wherein the hollow passages of the microneedles can be connected to the solution passage of the microneedle substrate. The transdermal drug administration apparatus having microneedles can further comprise, outside the microneedle device, a skin anchoring portion for stretching the skin.

Moreover, a transdermal drug administration apparatus having microneedles according to the present invention comprises a microneedle device comprising a microneedle substrate having a plurality of microneedles capable of piercing the skin, a coating disposed on the microneedles and/or the microneedle substrate, the coating containing a dry drug, and a dissolving solution reservoir disposed on the microneedle device, the dissolving solution reservoir containing a dissolving solution for drug dissolution, wherein by pressing the dissolving solution reservoir, the dissolving solution reservoir is opened to supply the dissolving solution to the microneedle device, and further the microneedles pierce the skin, thereby allowing transdermal administration via the microneedles of the drug dissolved in the dissolving solution. In this context, the dissolving solution can be supplied to the microneedles via at least one solution passage formed on the microneedle substrate. Alternatively, the dissolving solution can be supplied to the microneedles from around the microneedle substrate. The transdermal drug administration apparatus having microneedles can further comprise an absorbent comprising a material capable of absorbing a liquid, in an area which is located between the microneedle device and the dissolving solution reservoir and at least corresponds to an area where the dissolving solution reservoir is opened.

Moreover, a method for applying a coating containing a drug according to the present invention is a method for applying a coating containing a drug to microneedles and/or a microneedle substrate in a microneedle device comprising a plurality of microneedles capable of piercing the skin and the microneedle substrate supporting the microneedles, comprising the steps of mixing a drug and a liquid to prepare a liquid composition, applying the liquid composition to the microneedles and/or the microneedle substrate, and drying the applied liquid composition.

A transdermal drug administration method according to the present invention comprises putting, onto the skin, an apparatus comprising a microneedle device having a plurality of microneedles capable of piercing the skin and a microneedle substrate supporting the microneedles, a coating disposed on the microneedles and/or the microneedle substrate, the coating containing a dry drug, a pad portion disposed on the microneedle device, and a dissolving solution reservoir disposed on the pad portion, the dissolving solution reservoir containing a dissolving solution for drug dissolution, and by pressing the dissolving solution reservoir, opening the dissolving solution reservoir to supply the dissolving solution to the pad portion and the microneedle device, and further piercing the skin with the microneedles, thereby allowing transdermal administration via the microneedles of the drug dissolved in the dissolving solution.

Moreover, a transdermal drug administration method according to the present invention comprises putting, onto the skin, an apparatus comprising a microneedle device having a plurality of microneedles capable of piercing the skin and a microneedle substrate supporting the microneedles, a coating disposed on the microneedles and/or the microneedle substrate, the coating containing a dry drug, and a dissolving solution reservoir disposed on the microneedle device, the dissolving solution reservoir containing a dissolving solution for drug dissolution, and by pressing the dissolving solution reservoir, opening the dissolving solution reservoir to supply the dissolving solution to the microneedle device, and further piercing the skin with the microneedles, thereby allowing transdermal administration via the microneedles of the drug dissolved in the dissolving solution.

In the present invention, the present apparatus, when used, is first attached to the skin such that the plurality of microneedles are brought into contact with the skin. Then, the sealed dissolving solution reservoir (container) which contains a dissolving solution is pressed, whereby the dissolving solution reservoir is opened. As a result, the dissolving solution flows into the microneedle device either via the pad portion or the absorbent or directly and dissolves therein the biologically active substance (drug). In addition, the microneedles pierce the skin by this pressing of the dissolving solution reservoir. The drug dissolved in the dissolving solution passes through the hole made by this piercing and is transdermally absorbed. Then, energy for promoting transdermal drug absorption is imparted thereto, if necessary.

The present invention can provide a transdermal drug administration apparatus having microneedles, which is capable of piercing the skin by a simple procedure in the transdermal administration of a biologically active substance (drug) and allows rapid absorption of the biologically active substance. In the transdermal administration of a biologically active substance, the microneedles coated with the drug pierce the skin, thereby allowing efficient transdermal administration (passive diffusion) of the biologically active substance. Accordingly, therapeutic effects brought about by iontophoretic administration can be enhanced.

BRIEF DESCRIPTION OF THE DRAWINGS

FIG. 2 is a diagram showing one embodiment of a transdermal drug administration apparatus having microneedles according to the present invention, wherein FIG. 2(a) is a plane view, FIG. 2(b) is a sectional view taken along the X-X line in FIG. 2(a), and FIGS. 2(c) and 2(d) are respectively a diagram showing the present apparatus in use.

FIG. 3 is a diagram showing an alternative embodiment of a transdermal drug administration apparatus having microneedles according to the present invention, wherein FIG. 3(a) is a plane view, FIG. 3(b) is a sectional view taken along the X-X line in FIG. 3(a), and FIGS. 3(c) and 3(d) are respectively a diagram showing the present apparatus in use.

FIG. 6 is a diagram showing a constitutional example of a microneedle device used in a transdermal drug administration apparatus having microneedles according to the present invention, wherein FIG. 6(a) is a general view, FIG. 6(b) is an enlarged view of the dotted circle in FIG. 6(a), FIG. 6(c) is a diagram showing the flow of a drug dissolved in a dissolving solution, and FIG. 6(d) is a fragmentary enlarged view showing a modification of a microneedle device.

Figure 1:
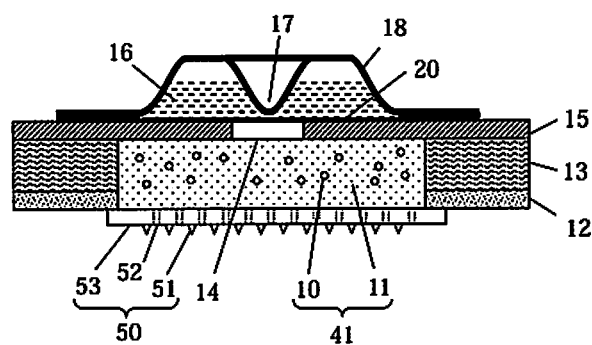
FIG. 1 is a schematic diagram showing one embodiment of a transdermal drug administration apparatus having microneedles according to the present invention.

DESCRIPTION OF SYMBOLS 10, 70 drug
11 absorbent containing dry drug
12 adhesive layer
13 wall material
14 opening
15 support
16 dissolving solution
17 protruding portion
18 dissolving solution reservoir
19 liner
20 diaphragm
25 electrode
26, 61 lead portion
31 absorbent free from drug
32 drug retainer
41 pad portion
50 microneedle device
51, 56 microneedles
52 solution passage
53 microneedle substrate
54 skin
55 direction of pressing
57 hollow passage
58 skin anchoring portion
59 plate-like reinforcement 60 sonic transducer
71 coating

BEST MODE FOR CARRYING OUT THE INVENTION

FIG. 1 is a schematic diagram showing one embodiment of a transdermal drug administration apparatus having microneedles according to the present invention. The present apparatus, as shown in the drawing, comprises a microneedle device 50 comprising a plurality of microneedles (needle portion) 51 capable of piercing the skin and a microneedle substrate 53 having at least one solution passage 52, a pad portion 41 disposed on the microneedle device 50, and a dissolving solution reservoir 18 disposed on the pad portion 41, wherein the dissolving solution reservoir 18 contains a dissolving solution 16 for drug dissolution and can be opened by pressing. A coating containing a dry drug is disposed on the microneedles 51 and/or the microneedle substrate 53 in the microneedle device 50. Examples of this coating will be described with reference to FIG. 6(*b*). Moreover, the pad portion 41, as shown in the present example, can comprise an absorbent 11 comprising a material capable of absorbing a liquid, and a drug 10. This drug 10 may be the same as or different from the drug used in the coating. The drug 10 can be provided in a drug retainer, as described later. A wall material 13 having an adhesive layer 12 on the undersurface is disposed around the absorbent 11. A support 15 having an opening 14 is disposed on the absorbent 11 and the wall material 13. A diaphragm 20 is disposed on the support 15. The diaphragm 20 may be formed separately from or integrally with the dissolving solution reservoir 18. The dissolving solution reservoir 18 has a protruding portion 17 for facilitating disrupting the diaphragm 20.

The present apparatus, when used, is attached to the skin such that the microneedles 51 are brought into contact with the skin. Then, the dissolving solution reservoir 18 is pressed, whereby the protruding portion 17 disrupts the diaphragm 20. As a result, the dissolving solution reservoir 18 is opened. In addition, the microneedles 51 pierce the skin by this pressing, thereby allowing transdermal absorption of the drug dissolved in the dissolving solution 16.

An electrode and a lead portion thereof are provided on the pad portion 41 of the present apparatus. As a result, the present apparatus can be used as an apparatus for an electrical drug administration system, for example, an apparatus for an iontophoresis system (iontophoresis electrode structure). When the present apparatus is used as a usual adhesive skin patch, this electrode and so on is unnecessary. Moreover, in the present apparatus, the pad portion 41 can separately comprise an absorbent comprising a material capable of absorbing a liquid, and a drug retainer containing the drug. In the present example, both the coating and the pad portion contain a drug. However, according to the present invention, the pad portion does not necessarily require containing a drug. It is only required that at least the coating should contain a drug. Specifically, this coating can be disposed on, for example, any one or some of the outer surface of the microneedles 51, the internal surface of their hollow passages, the upper surface, undersurface, or side of the microneedle substrate 53, and the internal surface of the solution passage 52 thereof. More preferably, the coating may be disposed on the outer surface of the microneedles 51, the internal surface of their hollow passages, or the undersurface of the microneedle substrate 53. Hereinafter, embodiments of the present invention will be described in detail.

Figure 2:
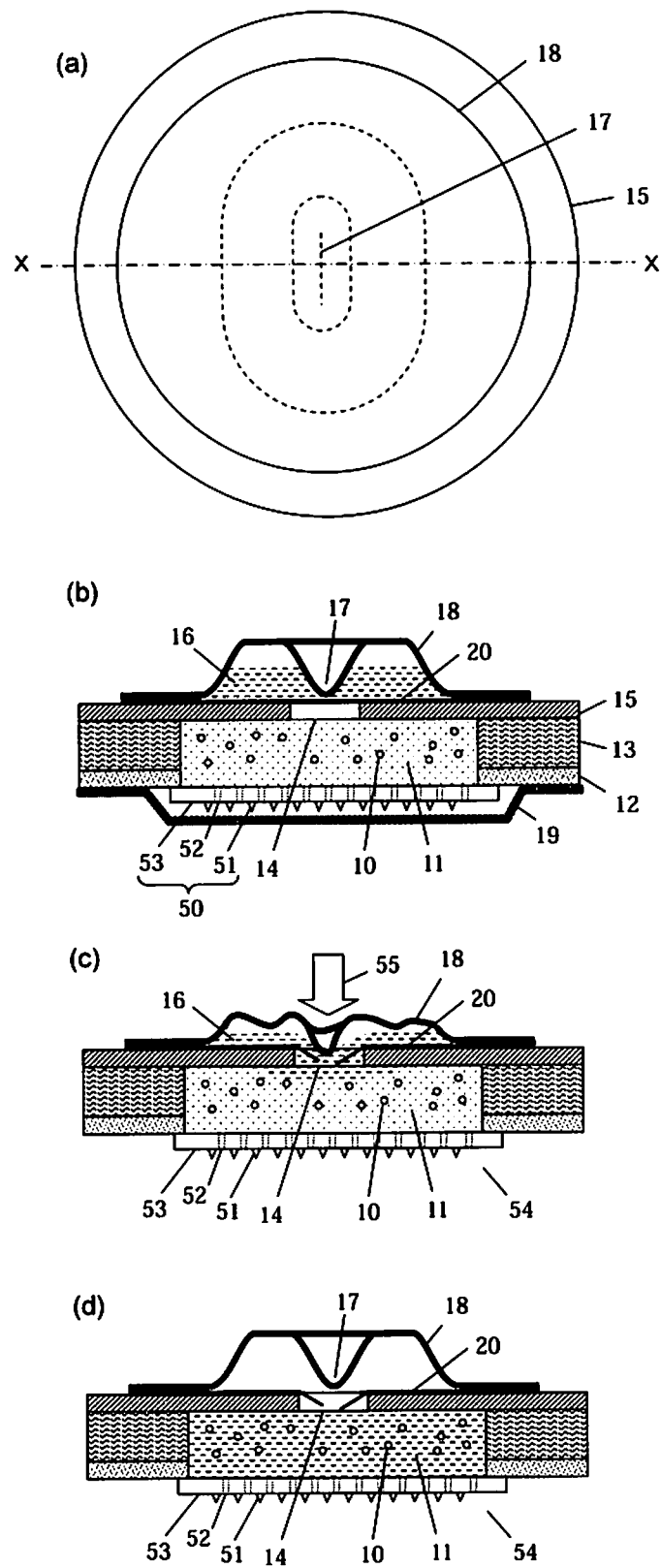

FIG. 2 is a diagram showing one embodiment of a transdermal drug administration apparatus having microneedles according to the present invention, wherein FIG. 2(*a*) is a plane view, FIG. 2(*b*) is a sectional view taken along the X-X line in FIG. 2(*a*), and FIGS. 2(*c*) and 2(*d*) are respectively a diagram showing the present apparatus in use. The apparatus of the present embodiment can be used as, for example, a usual adhesive skin patch. As shown in FIGS. 2(*a*) and 2(*b*), the apparatus comprises a microneedle device 50 comprising a microneedle substrate 53 having microneedles 51 on which a coating (not shown) containing a dry drug is disposed, and a plurality of solution passages 52, an absorbent 11 disposed on the microneedle device 50, wherein the absorbent 11 contains a dry drug 10 and comprises a material capable of absorbing a liquid, a wall material 13 disposed around the absorbent 11, wherein the wall material 13 has an adhesive layer 12 on the undersurface, a support 15 disposed on the absorbent 11 and the wall material 13, wherein the support 15 has an opening 14 in a central portion, a diaphragm 20 disposed on the support 15, and a dissolving solution reservoir 18 disposed on the diaphragm 20, wherein the dissolving solution reservoir 18 retains a dissolving solution 16 for dissolving a drug, between the dissolving solution reservoir 18 and the diaphragm 20 and has a protruding portion 17 for disrupting the diaphragm 20 by pressing. The protruding portion 17 has, for example, a linear tip shown in the drawing and is disposed in contact with or in proximity to the diaphragm 20. A liner 19 is removably attached on the underside of the microneedle device 50 and the adhesive layer 12.

In this context, the dissolving solution reservoir 18 and the diaphragm 20 may be formed separately from or integrally with each other. Moreover, the shape of the opening 14 in the support is not particularly limited. The shape of the opening 14 may be a shape that can fill the absorbent 11 with a solution and is preferably, for example, a circle. In this case, the size of the opening 14 is, for example, 2 mm to 10 mm, preferably 4 mm to 8 mm, in diameter, though depending on the size of the absorbent 11. The support 15 may be omitted, and the diaphragm 20 can instead have the functions of the support. In this case, the opening is not previously provided and is formed by the protruding portion in use. Moreover, the diaphragm 20 can also be formed as a portion of the dissolving solution reservoir 18.

As shown in FIG. 2(*c*), the present apparatus (adhesive skin patch), when used, is applied to a skin 54 after the removal of the liner 19. Then, the upper surface of the dissolving solution reservoir 18 is pressed in the direction of an arrow 55, thereby breaking the diaphragm 20 by the protruding portion 17. In this procedure, the diaphragm 20 is largely broken along the linear tip of the protruding portion 17. The dissolving solution 16 in the dissolving solution reservoir 18 flows into the absorbent 11 via the opening 14 in the support 15. This dissolving solution 16 infiltrates the absorbent 11 and the microneedle device 50 and uniformly activates the drugs. The whole apparatus is also pushed to the skin by this pressing of the dissolving solution reservoir 18 such that the microneedles 51 pierce the skin. As a result, the activated drugs permeate the skin via the microneedle substrate 53 and the microneedles 51. The dissolving solution reservoir 18 becomes empty after the supply of the dissolving solution 16 and recovers to the almost original shape as shown in FIG. 2(*d*).

The microneedle substrate 53 is constituted to have strength that does not cause the failure thereof during the pressing of the dissolving solution reservoir 18. The thickness of the microneedle substrate 53 is approximately 0.1 to 3 mm, more preferably 0.5 to 2 mm, for silicon or metal as a material thereof and is approximately 0.1 to 3 mm, more preferably 0.5 to 2 mm, for a polymer or the like as a material used in a substrate having a multilayer structure with a reinforcement. Thus, in the present invention, dissolving solution transport and skin piercing can be performed simultaneously by the pressing of the dissolving solution reservoir, that is, a pressing force can be conveyed directly as a piercing force. The piercing pressure of the microneedles can be adjusted by changing a breaking force on the diaphragm 20 exerted by the protruding portion 17 of the dissolving solution reservoir 18. Specifically, a force required to break the diaphragm by the pressing of the dissolving solution reservoir is appropriately in the range of, for example, 300 g to 3 kg/patch. This is a value based on the assumption that the needle preparation (microneedle substrate) has an area on the order of 1 to 4 cm$^2$ and the dissolving solution reservoir is pressed for 5 seconds. Thus, in the present invention, the dissolving solution reservoir is pressed, whereby the diaphragm provided between the dissolving solution reservoir and the absorbent is disrupted and whereby the microneedles pierce the skin, thereby allowing efficient delivery of the drug dissolved in the dissolving solution to the skin via the microneedle device.

Figure 3:
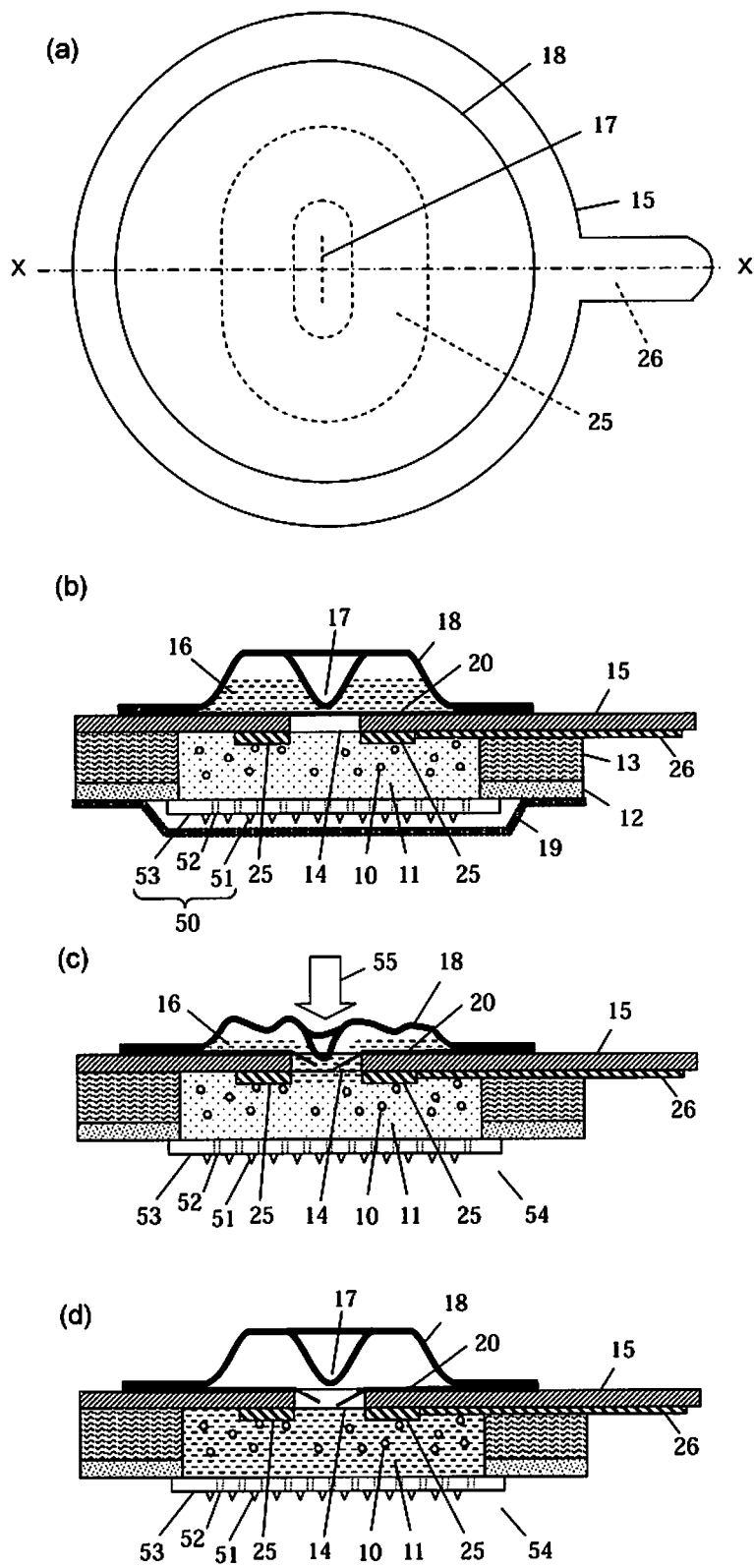

FIG. 3 is a diagram showing an alternative embodiment of a transdermal drug administration apparatus having microneedles according to the present invention, wherein FIG. 3($a$) is a plane view, FIG. 3($b$) is a sectional view taken along the X-X line in FIG. 3($a$), and FIGS. 3($c$) and 3($d$) are respectively a diagram showing the present apparatus in use. In FIG. 3, the same reference numerals designate the same components as those in FIG. 2. The present embodiment is different from the embodiment of FIG. 2 in that an electrode 25 for supplying electrical energy from outside is provided on the absorbent 11. The electrode 25 is connected to a lead portion 26. As a result, the apparatus of the present embodiment can be used as an apparatus for an electrical drug administration system, for example, an apparatus for an iontophoresis system (iontophoresis electrode structure). For the rest, the present embodiment is the same as the embodiment of FIG. 2.

The electrode 25 and the lead portion 26 are prepared, for example, by printing on the undersurface of the support 15. The electrode 25 is connected via the lead portion 26 to either output terminal (e.g., +electrode) of a power supply (not shown). The other output terminal (e.g., −electrode) of the power supply is connected to a counter (not shown). The counter can be constituted in the same way as the present transdermal drug administration apparatus. However, the counter does not necessarily require containing a drug. The power supply imparts a voltage or current for iontophoresis to between the present transdermal drug administration apparatus and the counter.

The present apparatus (iontophoresis electrode structure), when used, is applied to a skin 54 after the removal of the liner 19. Then, the upper surface of the dissolving solution reservoir 18, as shown in FIG. 3($c$), is first pressed in the direction of an arrow 55, thereby breaking the diaphragm 20 by the protruding portion 17. In this procedure, the diaphragm 20 is largely broken along the linear tip of the protruding portion 17. The dissolving solution in the dissolving solution reservoir 18 flows into the absorbent 11 via the opening 14 in the support 15. This dissolving solution infiltrates the absorbent 11 and the microneedle device 50 and uniformly activates the drugs. The whole apparatus is also pushed to the skin by this pressing of the dissolving solution reservoir 18 such that the microneedles 51 pierce the skin. Then, the power supply (not shown) is turned on to operate the iontophoresis system. As a result, the activated drugs permeate the skin via the microneedle substrate 53 and the microneedles 51. The dissolving solution reservoir 18 becomes empty after the supply of the dissolving solution 16 and recovers to the almost original shape as shown in FIG. 3($d$). Thus, in the present invention, the dissolving solution reservoir is pressed, whereby the diaphragm provided between the dissolving solution reservoir and the absorbent is disrupted and whereby the microneedles pierce the skin, thereby allowing efficient delivery of the drug dissolved in the dissolving solution to the skin via the microneedle device.

Figure 4:
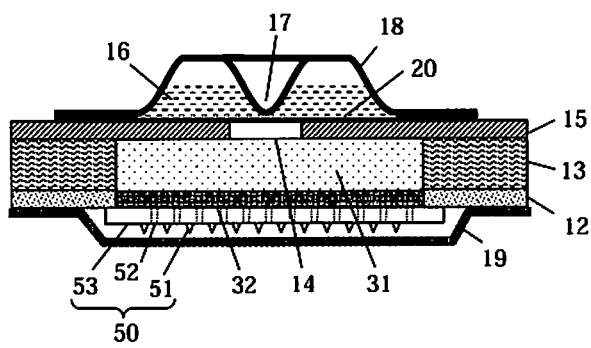
FIG. 4 is a diagram showing an alternative embodiment of a transdermal drug administration apparatus having microneedles according to the present invention.

FIG. 4 is a diagram showing an alternative embodiment of a transdermal drug administration apparatus having microneedles according to the present invention. In the apparatus of the present embodiment, the absorbent 11 containing a drug of FIG. 2 is separated into two portions an absorbent 31 free from a drug and a drug retainer 32 containing a drug. For the rest, the present embodiment is the same as the embodiment of FIG. 2. The reason why the absorbent 31 and the drug retainer 32 are separately provided is that a drug is brought at a high concentration into contact with the living body, thereby exerting the highest absorption of the drug.

Figure 5:
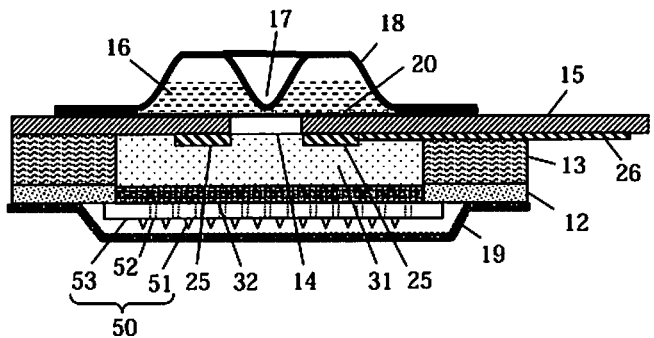
FIG. 5 is a diagram showing an alternative embodiment of a transdermal drug administration apparatus having microneedles according to the present invention.

FIG. 5 is a diagram showing an alternative embodiment of a transdermal drug administration apparatus having microneedles according to the present invention. In FIG. 5, the same reference numerals designate the same components as those in FIGS. 3 and 4. The present embodiment is different from the embodiment of FIG. 4 in that an electrode 25 for supplying electrical energy from outside is provided on the absorbent 11. The electrode 25 is connected to a lead portion 26. As a result, the apparatus of the present embodiment can be used as an apparatus for an electrical drug administration system, for example, an apparatus for an iontophoresis system (iontophoresis electrode structure). For the rest, the present embodiment is the same as the embodiments of FIGS. 3 and 4.

Figure 6:
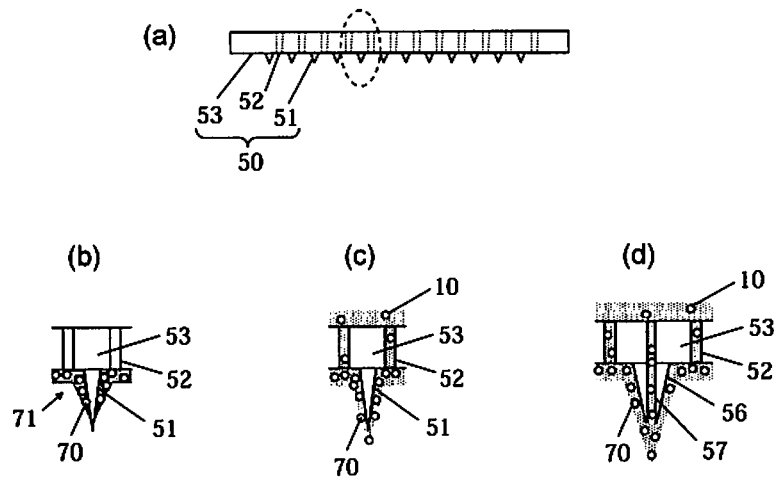

FIG. 6 is a diagram showing a constitutional example of a microneedle device used in a transdermal drug administration apparatus having microneedles according to the present invention, wherein FIG. 6($a$) is a general view, FIG. 6($b$) is an enlarged view of the dotted circle in FIG. 6($a$), FIG. 6($c$) is a diagram showing the flow of a drug dissolved in a dissolving solution, and FIG. 6($d$) is a fragmentary enlarged view showing a modification of a microneedle device. As shown in FIG. 6($a$), a microneedle device 50 comprises a microneedle substrate 53 having a plurality of microneedles 51 capable of piercing the skin and a plurality of solution passages 52. In the present example, the surface of the microneedles 51 and the undersurface of the microneedle substrate 53, as shown in FIG. 6($b$), comprise a coating 71 containing a dry drug 70. Dissolved drugs 10 and 70, as shown in FIG. 6($c$), flow to the skin together with the dissolving solution along the microneedles 51. Moreover, as shown in FIG. 6($d$), a hollow passage 57 capable of delivering a drug may be formed in the longitudinal direction of the microneedles 56, wherein the hollow passages 57 of the microneedles may be connected to the solution passage 52 of the microneedle substrate.

Figure 7:
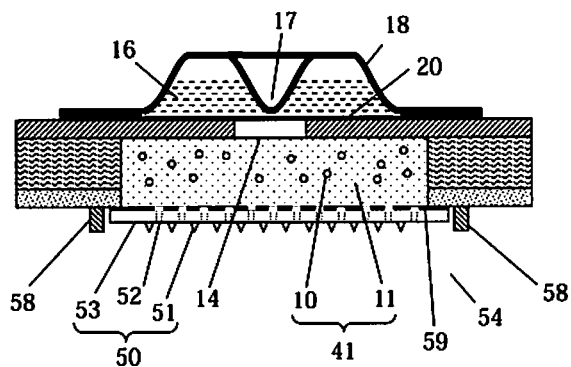
FIG. 7 is a diagram showing an alternative embodiment of a transdermal drug administration apparatus having microneedles according to the present invention.

FIG. 7 is a diagram showing an alternative embodiment of a transdermal drug administration apparatus having microneedles according to the present invention. The apparatus of the present embodiment comprises, outside the microneedle device 50 of FIG. 1, a skin anchoring portion 58 for stretching the skin in an area pierced by microneedles. Furthermore, the microneedle device 50 comprises a plate-like reinforcement 59 having at least one solution passage. For the rest, the present embodiment is the same as the embodiment of FIG. 1. The height of the skin anchoring portion 58 is preferably larger than the thickness of the microneedle device 50. Moreover, the skin anchoring portion 58 can be provided in the adhesive layer 12 outside the microneedle device 50, but not limited to this. The shape thereof can be a ring, for example, an O-ring, but not limited to this. The shape may be a portion of a ring or does not have to be a ring. The plate-like reinforcement 59 in the microneedle device 50 is disposed on, for example, the microneedle substrate 53. This reinforcement is provided for reinforcing the microneedle substrate 53 to prevent the failure thereof. The present embodiment has the advantages that the skin anchoring portion 58 stretches the skin and therefore facilitates skin piercing by the microneedles 51, and the plate-like reinforcement 59 can solidify the microneedle device 50. In the present embodiment, the apparatus shown is the apparatus of FIG. 1 provided with both the skin anchoring portion 58 and the plate-like reinforcement 59. However, the apparatus may be provided with only one of them. Likewise, the apparatuses of FIGS. 2 to 5 can also be provided with the skin anchoring portion 58 and/or the plate-like reinforcement 59.

Figure 8:
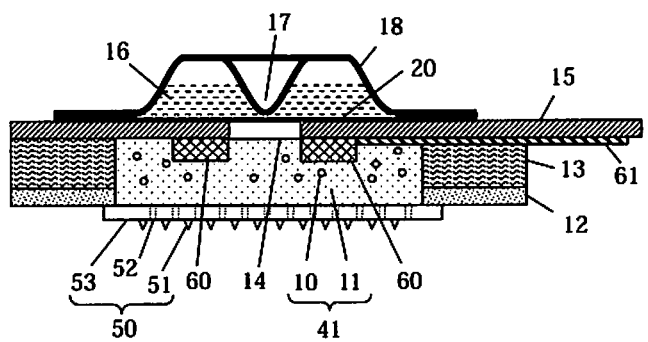
FIG. 8 is a diagram showing an alternative embodiment of a transdermal drug administration apparatus having microneedles according to the present invention.
Figure 9:
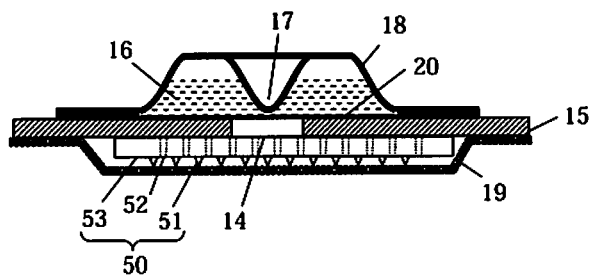
FIG. 9 is a diagram showing an alternative embodiment of a transdermal drug administration apparatus having microneedles according to the present invention.

FIG. 8 is a diagram showing an alternative embodiment of a transdermal drug administration apparatus having microneedles according to the present invention. The apparatus of the present embodiment comprises on the pad portion 41 of FIG. 1, a sonic transducer 60 for supplying sonic vibration energy from outside, and a lead portion 61 for external power connection connected to the sonic transducer 60. The sonic transducer 60 is, for example, doughnut-shaped and is disposed to surround the opening in the support 15. The sonic transducer 60 comprises, for example, a material such as ceramics and has an oscillation frequency of 1 KHz to 5 MHz and intensity up to 3.0 mW/cm$^2$. The sonic transducer 60 is effective for promoting the diffusion of the drug 10. FIG. 9 is a diagram showing an alternative embodiment of a transdermal drug administration apparatus having microneedles according to the present invention. The apparatus of the present embodiment comprises a microneedle device 50 comprising a microneedle substrate 53 having a plurality of macroneedles 51 capable of piercing the skin, and a dissolving solution reservoir 18 disposed on the microneedle device 50, wherein the dissolving solution reservoir 18 contains a dissolving solution 16 for drug dissolution. In the present embodiment, at least one solution passage 52 is formed in the microneedle substrate 53. A coating containing a dry drug is disposed on the microneedle device 50. This coating is disposed on, for example, any one or some of the outer surface of the microneedles 51, the internal surface of their hollow passages, the upper surface, undersurface, or side of the microneedle substrate 53, and the internal surface of the solution passage 52 thereof. The present apparatus, when used, is applied to the skin after the removal of a liner 19. A protruding portion 17 in the dissolving solution reservoir 18 is pressed, whereby a diaphragm 20 is disrupted, thereby opening the dissolving solution reservoir 18. The dissolving solution 16 is supplied to the microneedle device 50 via an opening 14 formed in a support 15. As a result, the dissolving solution 16 is supplied to the microneedles 51 via the solution passage 52 formed in the microneedle substrate 53. In addition, the microneedles 51 pierce the skin by this pressing, thereby allowing transdermal absorption of the drug dissolved in the dissolving solution. In this drawing, an adhesive layer for retaining the liner 19 in the support 15 before use and a drug disposed on the microneedle device 50 are omitted from the drawing for the sake of simplification.

Figure 10:
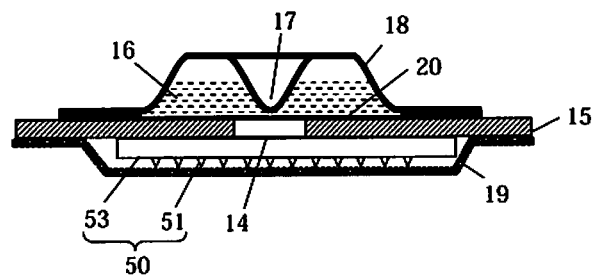
FIG. 10 is a diagram showing an alternative embodiment of a transdermal drug administration apparatus having microneedles according to the present invention.

FIG. 10 is a diagram showing an alternative embodiment of a transdermal drug administration apparatus having microneedles according to the present invention. The apparatus of the present embodiment is different from the embodiment of FIG. 9 in that no solution passage is formed in the microneedle substrate 53. For the rest, the present embodiment is the same as the embodiment of FIG. 9. Specifically, in the present embodiment, the present apparatus, when used, is applied to the skin after the removal of the liner 19. The protruding portion 17 of the dissolving solution reservoir 18 is pressed, whereby the diaphragm 20 is disrupted, thereby opening the dissolving solution reservoir 18. The dissolving solution 16 is supplied to the microneedle device 50 via the opening 14 formed in the support 15. In this supply, the dissolving solution 16 is spread over the microneedle substrate 53 facing the opening 14 and supplied to the microneedles 51 from around the microneedle substrate 53. In addition, the microneedles 51 pierce the skin by this pressing, thereby allowing transdermal absorption of the drug dissolved in the dissolving solution. The microneedle substrate 53 of the present embodiment is free from the solution passage 52 formed in the embodiment of FIG. 9 and therefore has the advantage that it is easily prepared by virtue of its simple structure. However, a groove for passing the dissolving solution therethrough may be formed in at least one of the upper surface and undersurface of the macroneedle substrate 53 to facilitate the flow of the dissolving solution 16 to the microneedles 51 from around the microneedle substrate 53. Moreover, a predetermined gap may be provided between the dissolving solution reservoir 18 and the microneedle substrate 53 to facilitate the spread of the dissolving solution 16 without bringing the dissolving solution reservoir 18 into contact with the microneedle substrate 53.

Figure 11:
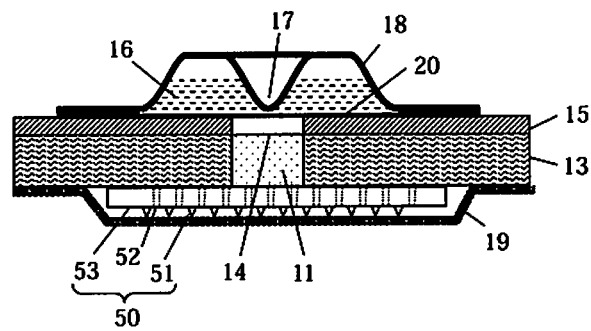
FIG. 11 is a diagram showing an alternative embodiment of a transdermal drug administration apparatus having microneedles according to the present invention.

FIG. 11 is a diagram showing an alternative embodiment of a transdermal drug administration apparatus having microneedles according to the present invention. The apparatus of the present embodiment is different from the embodiment of FIG. 9 in that the apparatus of the present embodiment comprises an absorbent 11 comprising a material capable of absorbing a liquid, in an area which is located between the microneedle device 50 and the dissolving solution reservoir 18 and at least corresponds to an area where the dissolving solution reservoir 18 is opened, wherein the absorbent 11 is surrounded by a wall material 13. For the rest, the present embodiment is the same as the embodiment of FIG. 9. Specifically, in the present embodiment, the present apparatus, when used, is applied to the skin after the removal of the liner 19. The protruding portion 17 of the dissolving solution reservoir 18 is pressed, whereby the diaphragm 20 is disrupted, thereby opening the dissolving solution reservoir 18. The dissolving solution 16 is supplied to the microneedle device 50 via the opening 14 formed in the support 15 and the absorbent 11 provided in an area corresponding thereto. As a result, the dissolving solution 16 is supplied to the microneedles 51 via the solution passage 52 formed in the microneedle substrate 53. In addition, the microneedles 51 pierce the skin by this pressing, thereby allowing transdermal absorption of the drug dissolved in the dissolving solution. In the present embodiment, the microneedle substrate 53 having the solution passage 52 formed therein is used, as in the embodiment of FIG. 9, but not limited to this. For example, the microneedle substrate 53 having no solution passage formed therein can also be used, as in the embodiment of FIG. 10. In this case, the dissolving solution 16 is supplied to the microneedles 51 from around the microneedle substrate 53, as described above.

In the embodiments shown in FIGS. 9 to 11, the apparatus can also comprise, on the microneedle device or on the absorbent, an electrode for supplying electrical energy from outside (not shown). As a result, the apparatus can be used as an apparatus for an electrical drug administration system, for example, an apparatus for an iontophoresis system (iontophoresis electrode structure). Alternatively, the apparatus can comprise, on the macroneedle device or on the absorbent, a sonic vibration for supplying sonic vibration energy from outside. Moreover, the plurality of microneedles can have a hollow passage capable of delivering a drug in the longitudinal direction thereof, wherein the hollow passages of the microneedles can be connected to the solution passage of the microneedle substrate. Furthermore, the apparatus can comprise, outside the microneedle device, a skin anchoring portion for stretching the skin.

In the transdermal drug administration apparatus having microneedles according to the present invention, members or components below can be used.

The biologically active substance (drug) can be selected from various kinds of drugs according to a therapeutic purpose. For example, the biologically active substance (drug) is not particularly limited by the type of an agent, the type of a salt, indications for each agent, and the like, as long as it is a compound having pharmacological activity. For example, antibiotics, antifungal agents, antitumor agents, cardiacs, therapeutic agents for arrhythmia, vasodilators, hypotensive agents, diuretics, antihypertensive diuretics, cardiovascular agents, antiplatelet drugs, hemostatics, hypolipidemic agents, antipyretic/analgesic/antiphlogistic agents, antirheumatic agents, relaxants, antitussives and expectorants, antiulcer agents, sedatives, antiepileptics, antidepressants, antiallergic agents, therapeutic agents for diabetes, antitubercular agents, hormone agents, narcotic antagonists, inhibitors of bone resorption, angiogenesis inhibitors, and local anesthetics are used.

When the apparatus is used in an iontophoresis system, the drug can be selected from various kinds of drugs according to a therapeutic purpose, as described above. The present apparatus is particularly useful for a drug with strict acceptable accuracy of a dose in drug administration using iontophoresis. The present apparatus can be used with safe for a drug having a narrow margin between an effective blood level and a concentration causing side effects, such as insulin. Moreover, in other drugs having a relatively wide margin between an effective blood level and a concentration causing side effects, the minimization of electrical error factors is also important for obtaining high safety and effectiveness of the drugs. Moreover, in addition to the drug, a dissolution rate modifier for drugs, an additive for stabilization, an anti-adsorption agent, and the like can be added thereto. A pH adjustor and an absorption promoter are appropriately retained in a dry state.

The absorbent is selected from materials capable of favorably absorbing a liquid. Examples thereof include polyester (polyethylene terephthalate), polysaccharides or cellulose derivatives (rayon and cotton), polyamide (nylon), porous materials such as nonwoven fabrics, woven fabrics, gauze, or sponge, hydrophilic polymers (agar, agarose, alginic acid, xanthan gum, guar gum, dextran, dextrin, pullulan, chitosan, gelatin, carboxyvinyl polymers, polyacrylate, carboxymethylcellulose salts, polyoxyalkylene, polyvinyl alcohol, polyvinyl pyrrolidone, and polyacrylamide), and ion-exchange resins (amberlite, diaion, and cholestyramine). Preferably, the absorbent is a nonwoven fabric mainly composed of rayon.

For example, a hydrophilic membrane or rigid material (e.g., ceramics, metals, or polymer materials) having a drug-permeable passage formed therein can be used as the drug retainer. Alternatively, a porous membrane or ion-exchange membrane containing a drug can be used. Examples of the porous membrane include polyolefin (PE and PP), cellulose, cellulose acetate, polyethylene terephthalate (PET), and nylon. Examples of the ion-exchange membrane include cation-exchange membranes, anion-exchange membranes, and composite charged membranes. Preferably, the drug retainer is a nylon-based cation-exchange membrane.

The wall material is selected from water-impermeable materials. Examples thereof include polyolefin (PE, PP, etc.) foams, polyurethane foams, polystyrene foams, rubber (polybutylene, etc.) foams, polyvinyl acetate (EVA) foams, and polyvinyl chloride (PVC) foams. Preferably, the wall material is, for example, a polyolefin foam.

Examples of the adhesive layer include natural rubbers, styrene-isoprene-styrene block copolymers, styrene-butadiene rubbers, styrene-isoprene rubbers, polyisobutylene, polyisoprene, polyacrylate, and silicon rubbers. Preferably, the adhesive layer is polyacrylate.

The support is selected from water-impermeable materials. Examples thereof include polyolefin, polyurethane, polystyrene, rubbers, EVA, PVC, and PET.

Examples of the dissolving solution reservoir include a molded sheet obtained by molding, into a dome-like shape, a sheet material made of PET, PVC, PVDC (polyvinylidene chloride), PP, PE, polystyrene, cyclic polyolefin (COC), aluminum (Al), and a multilayer thereof and forming a convex protruding portion in the inside thereof, sheets (PCTFE/PP-based, PCTFE/PVC-based, or cyclic polyolefin/PP-based) having high barrier properties, and Al-deposited or $SiO_2$-deposited sheets. The convex protruding portion of the dissolving solution reservoir is pressed, whereby at least one site in the diaphragm or a multilayer of the diaphragm and the support is disrupted. If the convex protruding portion is conically shaped, an area disrupted by this protruding portion is a small spot, through which the dissolving solution poorly permeate the absorbent. It is preferred that the convex breaking-through portion (tip of the protruding portion) should be linear or planar. The material may be PCTFE ($-CF_2-CFCl-$)$_n$ poly(chloro-trifluoroethylene) or a COC cyclic polyolefin copolymer. The thickness of the sheet is set to, for example, 100 to 500 µm. Preferably, for example, a PP—, PP/COC/PP—, or PCTFE/PP-based sheet is used as the dissolving solution reservoir.

Examples of the diaphragm (membrane to be broken or disrupted by the protruding portion) include Al, PP, PE, and a multilayer thereof. It is preferred that a coating or the like should be applied, if necessary, to Al foil to prevent corrosion. The thickness of the diaphragm is set to, for example, 5 to 100 µm for Al and 15 to 50 µm for PP or PE.

Examples of the dissolving solution include water, alcohols, polyhydric alcohol, surfactants, sugars, pH adjustors (organic and inorganic acids and bases), salts, water-soluble polymers, solubilizers, absorption promoters, fats and oils, and preservatives. Preferably, the dissolving solution is, for example, purified water, ethanol, glycerin, methylparaben, propylparaben, or propylene glycol. This dissolving solution is contained in the dissolving solution reservoir or can also be added dropwise beforehand to the skin.

Examples of the liner include PET, PEN (polyethylene naphthalate), PP, PE, paper, Al, and a multilayer thereof. Preferably, the liner is PET. It is also preferred that the liner should be subjected to surface treatment for mold release such as silicon treatment. Furthermore, it is preferred that the liner should be processed into a concave shape to prevent the liner from coming into contact with the microneedles.

Moreover, in the present invention, the apparatuses shown in the embodiments of FIGS. 2 and 3 can comprise a solution-permeable membrane on the undersurface of the absorbent containing a drug. The solution-permeable membrane is effective for retaining the absorbent and also acts as retaining means for containing a powdery substance. For example, a porous membrane or ion-exchange membrane can be used as the solution-permeable membrane. Examples of the porous membrane include PE, PP, cellulose, cellulose acetate, PET, and nylon. Examples of the ion-exchange membrane include cation-exchange membranes, anion-exchange membranes, and composite charged membranes. Preferably, the solution-permeable membrane is a nylon-based cation-exchange membrane. However, when the absorbent is an unwoven fabric, the apparatus may not comprise the solution-permeable membrane.

The microneedle device (needle-like structure) comprises microneedles (needle portion) capable of piercing the skin or mucous membrane and a microneedle substrate supporting the microneedles. A plurality of the microneedles are arranged on the substrate. In the present invention, the microneedles have a microstructure. Therefore, the size (height) of the microneedles is appropriately a length that is capable of piercing the stratum corneum of the skin and is preferably 50 µm to 1000 µm, more preferably 50 µm to 500 µm. The microneedles have a density at which they are located at a substantially equal distance from each other with respect to space. It is preferred that the microneedles should have a density of 100 to 10000 pieces/cm$^2$. In this context, the microneedle is a convex structure and refers to a needle shape in a broad sense or a structure including a needle shape, but not limited to a simple needle shape. Alternatively, the microneedles may have a blunt-tip shape and are therefore not limited to those having a sharp tip. The substrate is a foundation to support the microneedles. The form thereof is not limited. Examples of a material of the needle-like structure include silicon, silicon dioxide, ceramics, metals (stainless, titanium, nickel, molybdenum, chromium, cobalt, etc.), and plastics. Examples of a production method for the needle-like structure include wet or dry etching processing using a silicon substrate, precision machining (electric discharge machining, laser beam machining, dicing machining, etc.) using a metal or plastic, and mechanical milling. The microneedles and the microneedle substrate are integrally molded by these processing methods. Examples of a method for making the microneedles hollow include a method comprising fabricating the prepared microneedles by laser beam machining or the like.

In the present invention, the microneedles can be coated with an active drug by use of purified water, lower alcohol, polyhydric alcohol, and/or a polymer carrier (coating agent). It is preferred that the polymer carrier used should comprise at least one selected from polyethylene oxide, hydroxypropylmethylcellulose, polyethylene glycol, polyvinyl alcohol, dextran, polyvinyl pyrrolidone, and chondroitin. For example, the whole surface of the microneedles is coated with such a coating agent. Then, the coating agent is dried. The microneedles with the dry drug coating thus prepared pierce the skin in use, thereby allowing transdermal absorption of the drug dissolved in the dissolving solution through the hole made by this piercing. Then, energy for promoting transdermal drug absorption is imparted thereto, if necessary.

Moreover, it is preferred that the coating polymer carrier should have a concentration of 1 to 70% by weight, particularly 3 to 20% by weight. Moreover, this coating carrier should have a viscosity to some extent to prevent dripping and should have a viscosity on the order of 100 to 50,000 cps, more preferably a viscosity of 300 to 10,000 cps, most preferably a viscosity of 500 to 5,000 cps.

Moreover, the thickness of the coating is less than 50 µm, most preferably less than 25 µm, that is, 1 to 10 µm. In general, the thickness of the coating is an average thickness measured over the surface of the microneedles after drying. The thickness of the coating can generally be increased by applying thereto several films (coatings) of the coating carrier. The coating can be formed by drying the films during continuous coating procedures. The coating is applied to the microneedles by use of a known method and formed by drying.

A liquid composition used for coating the microneedles is prepared by mixing a biocompatible carrier, a beneficial active substance (drug) to be delivered, and, optionally, any coating auxiliary substance, with a volatile liquid. The volatile liquid can be water, dimethyl sulfoxide, dimethylformamide, ethanol, isopropyl alcohol, and a mixture thereof. Among them, water is most preferable. The coating solution or suspension in a liquid state can typically have a beneficial biologically active substance concentration of approximately 0.1 to 40% by weight, preferably 1 to 30% by weight, more preferably 3 to 20% by weight. The coating is deposited on the surface of the microneedles and then dried by use of a known drying method such as air drying, vacuum drying, freeze drying, and/or a combination thereof. The term "dried" means that the coating is substantially free from the volatile liquid and should be interpreted to mean that the volatile liquid, if any, is 10% or less. When the aqueous coating solution or suspension is used, the coating typically retains a slight amount of water and more typically retains a water content in equilibrium with an atmosphere surrounding the microneedles.

Other known pharmaceutical auxiliary substances may be added to the coating, as long as they do not have a deleterious effect on the solubility and viscosity characteristics necessary for the coating and the physical integrity of the dried coating.

EXAMPLES

Hereinafter, Examples of the present invention will be described in detail. However, the present invention is not intended to be limited to Examples below.
(Effect of Using Drug Coating and Dissolving Solution in Combination)

Figure 12:
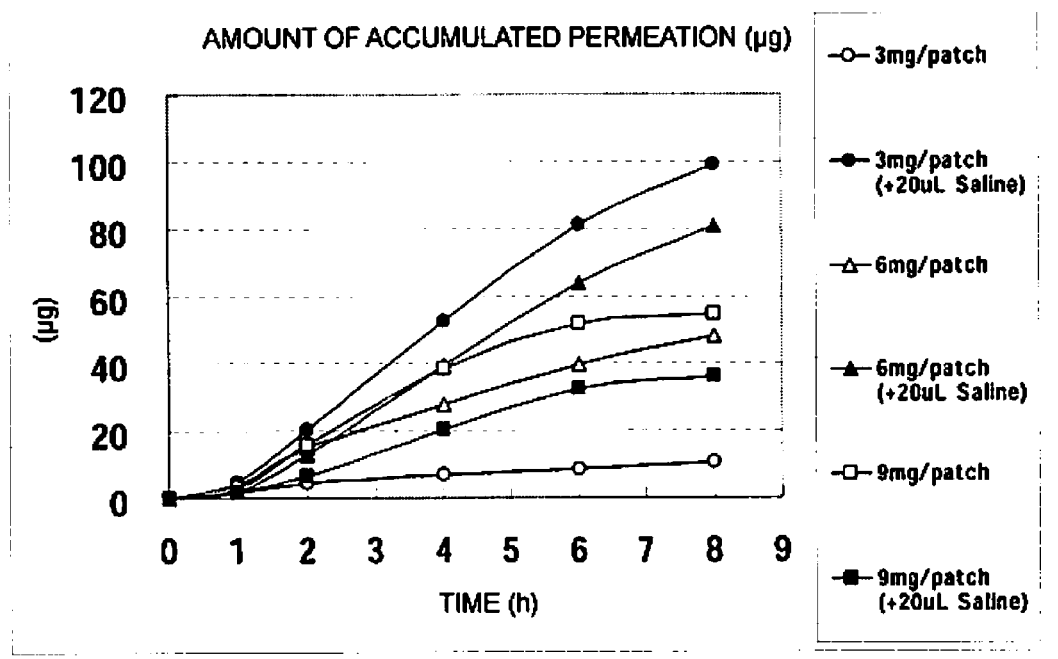
FIG. 12 is a graph showing data related to the effect of using a drug coating and a dissolving solution in combination.

A transdermal drug administration apparatus having microneedles of FIG. 9 was used. 30% aqueous solution was prepared with 100 mg of BSA (bovine serum albumin) and 150 mg of FITC-BSA (fluorescently labeled bovine serum albumin) as drugs and 350 µL of water and used as a mother liquid to prepare 10% and 20% aqueous solutions. The whole surface of microneedles was coated with each of the prepared 10 to 30% aqueous solutions in an amount of 30 µL/patch. The applied solution was dried at room temperature for 12 hours to prepare 3 kinds in total of coated microneedles (→3 mg/patch, 6 mg/patch, and 9 mg/patch) (FIG. 12).

The drug injection models used as controls are shown (FIG. 13), 15 µL of a 20% aqueous drug (FITC-BSA) solution was added to a dissolving solution without coating microneedles with the drug, and after coating with a 5% aqueous PVA203 solution in an amount of 30 µL/patch, the drug was added.

To measure the amount of permeation, the skin was ablated from the trunks of hairless mice and attached to vertical acrylic cells (2.54 cm$^2$) with the dermis facing a receptor layer. The cells were loaded in a thermostat set to 37° C. The transdermal drug administration apparatus having microneedles of the present invention was affixed to the stratum corneum. Sampling was conducted at a speed of 5.5 mL/hr. after 1 hour and 2 hours and subsequently at 2-hour intervals until the 8th hour. A phosphate-buffered saline (PBS) was used in the receptor layer. A drug content in the receptor solution obtained each time was measured with a fluorophotometer (excitation: 485, fluorescence: 538).

Animal type: hairless mice (n=3)
Receptor solution: 4 mL of PBS (Sampling volume: 200 µL/time)
Temperature: 37° C.
Area: 2.54 cm² (however, the M.N substrate itself is 1 cm²)
Dissolving solution: a saline was added dropwise from a dissolving solution reservoir.
PVA203: polyvinyl alcohol (partially saponified, polymerization degree: 300, KURARAY CO., LTD.)

Figure 13:
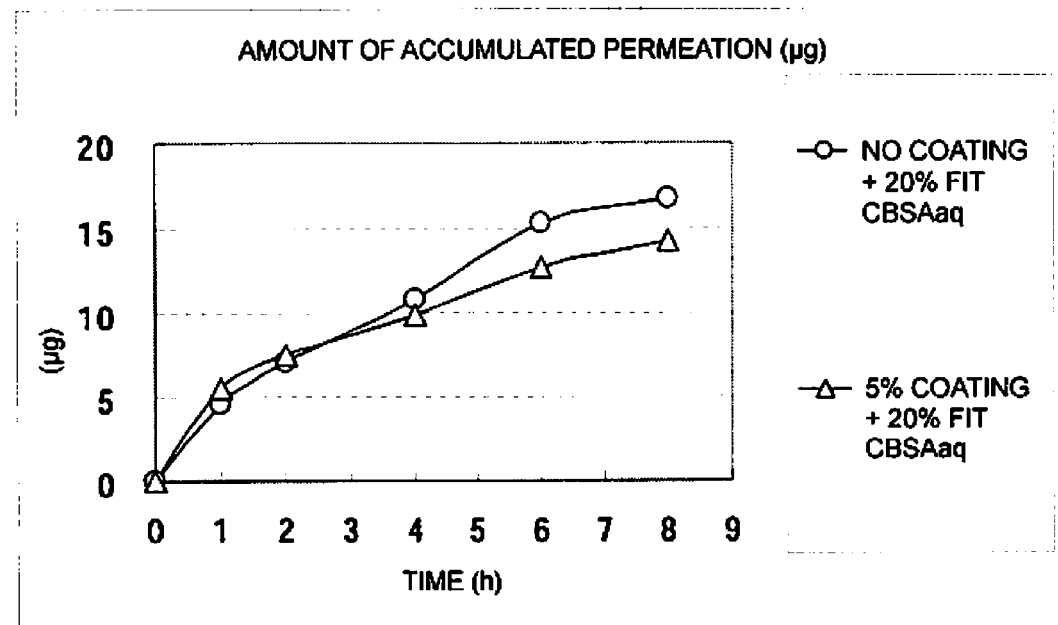
FIG. 13 is a graph showing data related to the effect of using a drug coating and a dissolving solution in combination.

Measurement results are shown in FIGS. 12 and 13.

The skin permeability of FITC-BSA was increased by using 20 µL of the dissolving solution in combination therewith. Thus, the relationship between the amount of the drug coating and the dissolving solution was studied. As a result, as shown in FIG. 12, the amount of the drug was adjusted to 3, 6, and 9 mg, and the amount of the dissolving solution was fixed to 20 µL. In this case, the effect of using the dissolving solution in combination therewith was highest in the amount of the drug of 3 mg. On the other hand, no synergistic effect brought about by the dissolving solution was observed in the amount of the drug of 9 mg. These results demonstrated that the balance between the amount of the drug and the amount of the dissolving solution is involved in promoting effects expected by the addition of the dissolving solution.

Moreover, as shown in FIG. 13, any of the controls give a low amount of permeation due to no drug coating applied to the needles.

(Effect of Using Drug Coating-Water-Soluble Polymer and Dissolving Solution in Combination)

A transdermal drug administration apparatus having microneedles of FIG. 9 was used. 400 mg of BSA (bovine serum albumin) and 400 mg of FITC-BSA (fluorescently labeled bovine serum albumin) as drugs were dissolved in 5 mL of water. Likewise, 800 mg of a polymer (PEO, PVA117) was dissolved in 5 mL of water. Both of the solutions were mixed in equal amounts to prepare a coating solution. The whole surface of microneedles was coated with 25 µL of the coating solution. The applied solution was dried with a drier for 30 minutes. Moreover, no polymer was added to a coating agent containing only water.

To measure the amount of permeation, the skin was ablated from the trunks of hairless mice and attached to vertical acrylic cells (2.54 cm²) with the dermis facing a receptor layer. The cells were loaded in a thermostat set to 37° C. The transdermal drug administration apparatus having microneedles of the present invention was affixed to the stratum corneum. Sampling was conducted at a speed of 5.5 mL/hr. after 1 hour and 2 hours and subsequently at 2-hour intervals until the 8th hour. A phosphate-buffered saline (PBS) was used in the receptor layer. A drug content in the receptor solution obtained each time was measured with a fluorophotometer (excitation: 496, fluorescence: 517).
Animal type: hairless mice (n=3)
Receptor solution: 4 mL of PBS (Sampling volume: 500 µL/time)
Temperature: 37° C.
Area: 2.54 cm² (however, the M.N substrate itself is 1 cm²)
Dissolving solution: a saline was added dropwise from a dissolving solution reservoir.
PEO: polyethylene oxide (molecular weight: 900,000, concentration: 2.5%)
PVA117S: polyvinyl alcohol (completely saponified, KURARAY CO., LTD.)

Figure 14:
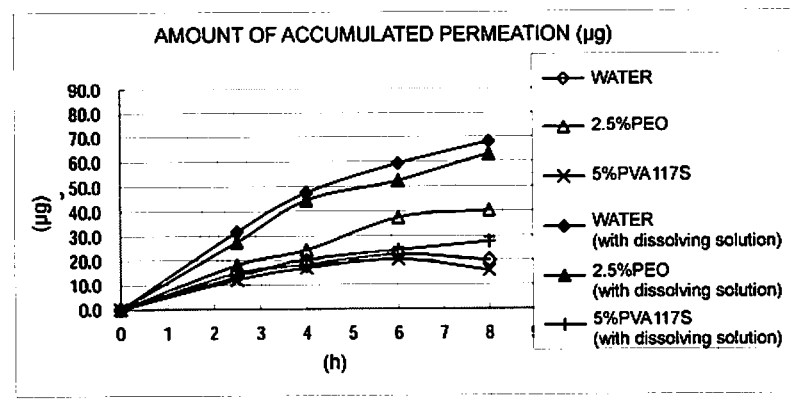
FIG. 14 is a graph showing data related to the effect of using a drug coating-water-soluble polymer and a dissolving solution in combination.

Measurement results are shown in FIG. 14.

When the water-soluble polymer polyethylene oxide (molecular weight: 900,000) is mixed into coating composition or when only water but no polymer is mixed into coating composition, the skin permeability of FITC-BSA, as shown in FIG. 14, is increased by using 20 µL of the dissolving solution in combination therewith. Accordingly, this indicated that permeability may be adjusted with the dissolving solution. On the other hand, when the poorly soluble polymer PVA117 was mixed into coating composition, no skin permeability-promoting effects brought about by the addition of the dissolving solution were observed From these results, permeability-promoting effects can be expected by using the polymer having high solubility by itself or by adding the dissolving solution without use of such a polymer. These results also demonstrated that the use of the poorly soluble polymer gives no permeability-promoting effects even by the addition of the dissolving solution.
(Effect of Using Calcein Sodium Coating and Dissolving Solution in Combination)

A transdermal drug administration apparatus having microneedles of FIG. 9 was used. 70 mg of calcein sodium as a drug was mixed with 930 µL of a 5% aqueous polymer (polyvinyl pyrrolidone, dextran) solution. The whole surface of microneedles was coated with 25 µL of the solution. The applied solution was dried at room temperature for 12 hours. Moreover, no polymer was added to a coating agent containing only water.

To measure the amount of permeation, the skin was ablated from the trunks of hairless mice and attached to vertical acrylic cells (2.54 cm²) with the dermis facing a receptor layer. The cells were loaded in a thermostat set to 37° C. The transdermal drug administration apparatus having microneedles of the present invention was affixed to the stratum corneum. Sampling was conducted at a speed of 5.5 mL/hr. after 1 hour and 2 hours and subsequently at 2-hour intervals until the 6th hour. A phosphate-buffered saline (PBS) was used in the receptor layer. A drug content in the receptor solution obtained each time was measured with a fluorophotometer (excitation: 485, fluorescence: 538).
Animal type: hairless mice (n=3)
Receptor solution: 4 mL of PBS (Sampling volume: 200 µL/time)
Temperature: 37° C.
Area: 2.54 cm² (however, the M.N substrate itself is 1 cm²)
Dissolving solution: a saline was added dropwise from a dissolving solution reservoir.

Figure 15:
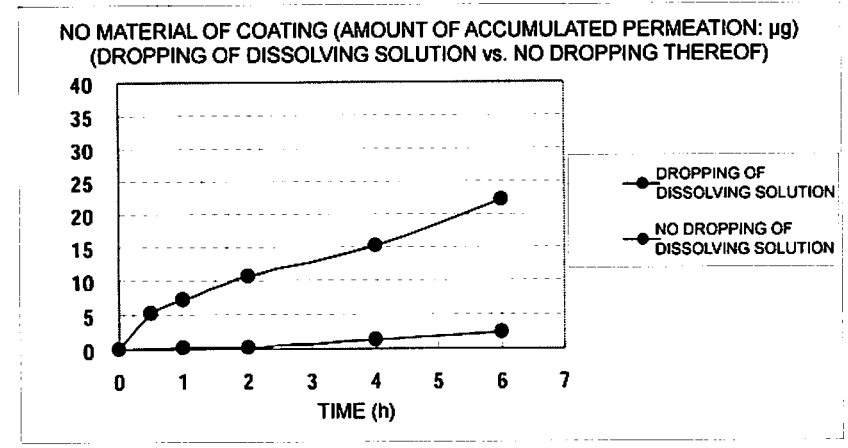
FIG. 15 is a graph showing data related to the effect of using a calcein sodium coating and a dissolving solution in combination.
Figure 16:
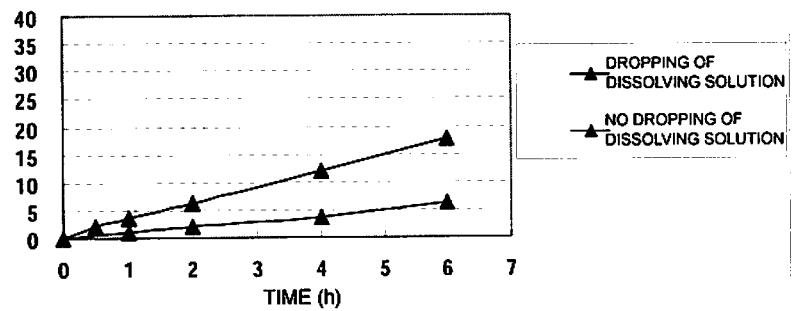
FIG. 16 is a graph showing data related to the effect of using a calcein sodium coating and a dissolving solution in combination.
Figure 17:
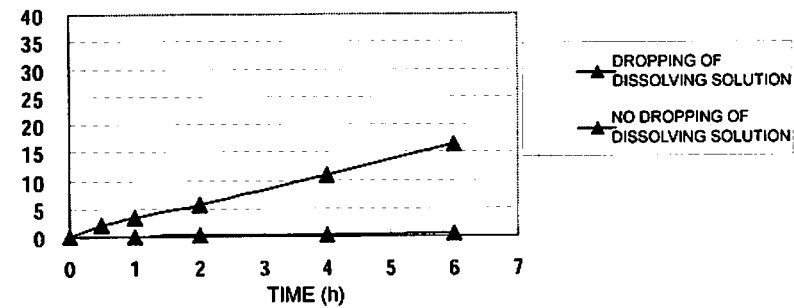
FIG. 17 is a graph showing data related to the effect of using a calcein sodium coating and a dissolving solution in combination.

Measurement results are shown in FIGS. 15, 16, and 17.

Permeability-promoting effects were observed in calcein sodium (molecular weight: 623), regardless of the presence or absence of the polymer, by the dropwise addition of the dissolving solution. Such promoting effects were also observed by using polyvinyl pyrrolidone and dextran in combination therewith.

INDUSTRIAL APPLICABILITY

The present invention relates to a transdermal drug administration apparatus for administrating a drug via the skin. Particularly, the present invention relates to a transdermal drug administration apparatus having microneedles comprising a plurality of microneedles capable of piercing the skin. This transdermal drug administration apparatus is industrially applicable. Moreover, in the transdermal administration of a poorly absorbable biologically active substance, the microneedles coated with the drug pierce the skin, thereby allowing efficient transdermal administration (passive diffusion) of the biologically active substance. Accordingly, therapeutic effects brought about by iontophoretic administration can be enhanced. Therefore, the transdermal drug administration apparatus of the present invention is largely industrially applicable.

The invention claimed is:

1. A transdermal drug administration method, comprising:
putting, onto the skin, an apparatus comprising a microneedle device having a plurality of microneedles capable of piercing the skin and a microneedle substrate supporting the microneedles; a coating disposed on the microneedles and/or the microneedle substrate, the coating containing a dry drug; a pad portion disposed on the microneedle device; and a dissolving solution reservoir disposed on the pad portion through a diaphragm, the dissolving solution reservoir containing a dissolving solution for drug dissolution and having a protruding portion formed therein, a tip of the protruding portion being linear or planar, the amount of the drug contained in the coating being 3-6 mg per 20 µL of the dissolving solution supplied to the microneedle substrate; and
by pressing the protruding portion of the dissolving solution reservoir to break the diaphragm, opening the dissolving solution reservoir to supply the dissolving solution to the pad portion and the microneedle device, and further piercing the skin with the microneedles, thereby allowing transdermal administration via the microneedles of the drug dissolved in the dissolving solution.

2. A transdermal drug administration method, comprising:
putting, onto the skin, an apparatus comprising a microneedle device comprising a plurality of microneedles capable of piercing the skin and a microneedle substrate supporting the microneedles; a coating disposed on the microneedles and/or the microneedle substrate, the coating containing a dry drug; and a dissolving solution reservoir disposed on the microneedle device through a diaphragm, the dissolving solution reservoir containing a dissolving solution for drug dissolution and having a protruding portion formed therein, a tip of the protruding portion being linear or planar, the amount of the drug contained in the coating being 3-6 mg per 20 µL of the dissolving solution supplied to the microneedle substrate; and
by pressing the protruding portion of the dissolving solution reservoir to break the diaphragm, opening the dissolving solution reservoir to supply the dissolving solution to the microneedle device, and further piercing the skin with the microneedles, thereby allowing transdermal administration via the microneedles of the drug dissolved in the dissolving solution.

* * * * *